(12) United States Patent
Farrow (10) Patent No.: US 9,730,472 B2
(45) Date of Patent: Aug. 15, 2017

(54) VAPORIZATION DEVICE AND METHOD OF PREPARATION AND USE

(71) Applicant: Darrin B. Farrow, Westlake, OH (US)

(72) Inventor: Darrin B. Farrow, Westlake, OH (US)

(*) Notice: Subject to any disclaimer, the term of this patent is extended or adjusted under 35 U.S.C. 154(b) by 0 days.

(21) Appl. No.: 14/501,153

(22) Filed: Sep. 30, 2014

(65) Prior Publication Data

US 2015/0090253 A1 Apr. 2, 2015

Related U.S. Application Data

(60) Provisional application No. 61/884,495, filed on Sep. 30, 2013, provisional application No. 61/884,512, filed on Sep. 30, 2013.

(51) Int. Cl.

| | |
|---|---|
| *A61M 15/00* | (2006.01) |
| *A61M 16/00* | (2006.01) |
| *A61M 11/00* | (2006.01) |
| *A24F 47/00* | (2006.01) |
| *A61M 15/06* | (2006.01) |
| *A61M 11/04* | (2006.01) |

(52) U.S. Cl.
CPC .......... *A24F 47/008* (2013.01); *A24F 47/004* (2013.01); *A61M 11/042* (2014.02); *A61M 15/0003* (2014.02); *A61M 15/0066* (2014.02); *A61M 15/06* (2013.01); *A61M 2202/04* (2013.01); *A61M 2202/06* (2013.01); *A61M 2205/502* (2013.01); *A61M 2205/583* (2013.01); *A61M 2205/6009* (2013.01); *A61M 2205/6045* (2013.01); *A61M 2205/8206* (2013.01)

(58) Field of Classification Search
CPC .... A24F 47/002; A24F 47/008; A24F 47/004; B65D 81/3283; A61M 15/00; A61M 16/12; A61M 15/009; A61M 16/18; A61M 16/16; A61M 15/006; A61M 15/0045; A61M 15/0003; B05B 11/062
USPC ............ 128/203.12, 203.15, 203.19, 203.21, 128/200.11–200.24; 604/58; 222/144.5, 222/145.5

See application file for complete search history.

(56) References Cited

U.S. PATENT DOCUMENTS

| | | | |
|---|---|---|---|
| 6,225,343 B1* | 5/2001 | Behl et al. .................... 514/468 |
| 6,684,880 B2* | 2/2004 | Trueba ..................... 128/200.16 |
| 7,348,140 B1* | 3/2008 | Weiner et al. ................ 435/6.14 |
| 2003/0017216 A1* | 1/2003 | Schmidt et al. ............... 424/725 |
| 2003/0072717 A1* | 4/2003 | Reinhold et al. ............... 424/46 |
| 2004/0192760 A1* | 9/2004 | Whittle et al. ................ 514/454 |

* cited by examiner

*Primary Examiner* — Peter S Vasat
*Assistant Examiner* — Ned T Heffner
(74) *Attorney, Agent, or Firm* — Bodi Law LLC (57) ABSTRACT

A vaporization device and its method of use, where the device can accommodate a plurality of formulations for dispensing by selecting the desired source. Such formulations can include different drug formulations for providing different effects on the user. Also, an indicator with specialized indicia can be provided to identify the source being dispensed.

23 Claims, 4 Drawing Sheets

VAPORIZATION DEVICE AND METHOD OF PREPARATION AND USE

CROSS-REFERENCES TO RELATED APPLICATIONS

This application claims the benefit of U.S. provisional application Ser. No. 61/884,495 filed on Sep. 30, 2013, incorporated herein by reference, and is also claims the benefit of U.S. provisional application Ser. No. 61/884,512 filed on Sep. 30, 2013, incorporated herein by reference.

BACKGROUND

Vaporizing and aerosol devices are used to dispense medications (e.g., nicotine, marijuana, opiates) or recreational substances (e.g., tobacco derivatives) to individual users. Vaporizing devices have also been used to extract essential oils from herbs or other plants, such as for cooking, or for Aromatherapy. Such devices often come in the form of a pen-like shape that is easy to store in a pocket or carrying bag. One such device is disclosed in U.S. Pat. App. Serial No. US 2013/0152922, incorporated herein by reference. Another such device is disclosed in U.S. Pat. Nos. 8,794,231, and 8,733,345 incorporated herein by reference.

Such pens can be used to dispense a formulation that includes concentrates (the drug, essential oil, or other ingredients to be dispensed) that are dissolved in a base solution such as propylene glycol or vegetable glycerin that acts as a hygroscopic (water-attracting) component to transform the solution into a vapor when heated. The device is provided with an atomizer with a heating element for vaporizing the solution. In some embodiments, the atomizer can be integrated into a metal cartridge or plastic/glass tank as a single unit, to form a cartomizer.

There are at least two heating methods that are used for vaporizing. A convection heating method can be used, in which case the solution never touches the heating element, but is instead, it's added to a polyfill medium, and then air heated by the heating element releases the active ingredients. Such convection systems incorporate a cartridge rather than a tank.

In contrast, conduction heating can be used. For this approach, the substance to be vaporized is placed on a metal element that is then heated to release the active ingredients. This approach can use a wick (e.g., silica) and a metal filament or coil (made of nickel, aluminum or steel), that may be encased in a small bowl (typically ceramic) and positioned in the center of a chamber or tank. The wick tank may be accessed by prying off a small plastic lid, which is used to contain the glycerin solution. For use with solid concentrates (such as wax, budder, etc.), the plastic lid could remain off.

Either approach may utilize the same base unit (e.g., powered by a lithium ion battery).

However, under current pen designs, when a user wants to change from one formulation (solution) to another, such as to go from a daytime formula to a nighttime formula, the user must either carry more than one pen, potentially leading to confusion as to which pen has which formula, or alternatively the user must swap out the cartridge, or empty and refill the tank, to utilize the second formula, which is inconvenient. Such approaches are not ideal.

SUMMARY

Provided are a plurality of example embodiments, including, but not limited to, a vapor dispensing device such as a vapor pen that utilizes two or more holding tanks or cartridges that the user can switch between so that a single pen can administer more than one formula (and hence dispense more than one drug or other substance, or more than one dosage, to the user).

Also provided is the above device where the holding tanks or cartridges are keyed to be installed in the device in a particular location based on the formulation provided in the respective tanks or cartridges.

Further provided is method of dispensing a vapor, comprising the steps of:

providing a portable vapor dispensing device adapted for personal use, said portable dispensing delivery device comprising: a dispensing component configured for dispensing a vaporized formulation orally to a user, at least one vaporizing component(s), a first container, a second container, and a selecting component configured for connecting the dispensing component to a selected one of the first container or the second container;

filling the first container with a first formulation for inducing a first physical effect in a user;

filling the second container with a second formulation for inducing a second physical effect in the user, said second physical effect being different than said first physical effect;

selecting one of the first formulation from the first container or the second formulation from the second container using the selecting component;

vaporizing, using the vaporizing component, the selected one of the first formulation or the second formulation; and dispensing, using the dispenser, the vaporized selected formulation in a manner that can be inhaled by the user.

Further provided is a method of dispensing a vapor, comprising the steps of:

providing a portable vapor dispensing device adapted for personal use, said portable dispensing delivery device comprising: a dispensing component configured for dispensing a vaporized formulation orally to a user, at least one vaporizing component(s), a first container, a second container, and a selecting component configured for connecting the dispensing component to a selected one of the first container or the second container;

providing the first container with a first drug formulation;

providing the second container with a second drug formulation different than the first drug formulation; and providing an indicator on the vapor dispensing device associated with the selecting component, said indicator having first indicia for identifying the first formulation from the first container and also having second indicial for identifying the second formulation from the second container.

Also provided are any of the above methods, wherein the portable vapor dispensing device has a chamber that is keyed for receiving the first container in a first location but not in a second location and the second container in the second location but not in the first location.

Also provided are any of the above methods, wherein the selecting component is provided with an indicator with indicia that identifies the formulation of the first container and also indicia that identifies the formulation of the second container.

Further provided is portable vapor dispensing device, comprising: a dispensing component configured for dispensing a vaporized formulation orally to a user, at least one vaporizing component(s), a chamber configured to receive a first container specially configured to be installed in a first location and a second container specially configured to be installed in a second location, such that said chamber is further configured such that said first container cannot be installed in said second location, and said second container cannot be installed in said first location; a selecting component configured for connecting the dispensing component to a selected one of the first container or the second container, wherein said vaporizing component vaporizes the selected one of the first formulation or the second formulation to provide to said dispensing component to dispense the vaporized selected formulation in a manner that can be inhaled by the user.

Also provided are any of the above methods or devices, with the device further comprising a third container including another drug formulation, where said selecting component is further configured for connecting the dispensing device to the drug formulation of the third container when selected.

Also provided are additional example embodiments, some, but not all of which, are described hereinbelow in more detail.

BRIEF DESCRIPTION OF THE DRAWINGS

The features and advantages of the example embodiments described herein will become apparent to those skilled in the art to which this disclosure relates upon reading the following description, with reference to the accompanying drawings, in which:

FIG. 7b shows a pair of cartridges each with necks keyed to fit respective receptors on the collar of FIG. 7a.

DETAILED DESCRIPTION OF THE EXAMPLE EMBODIMENTS

Figure 1:
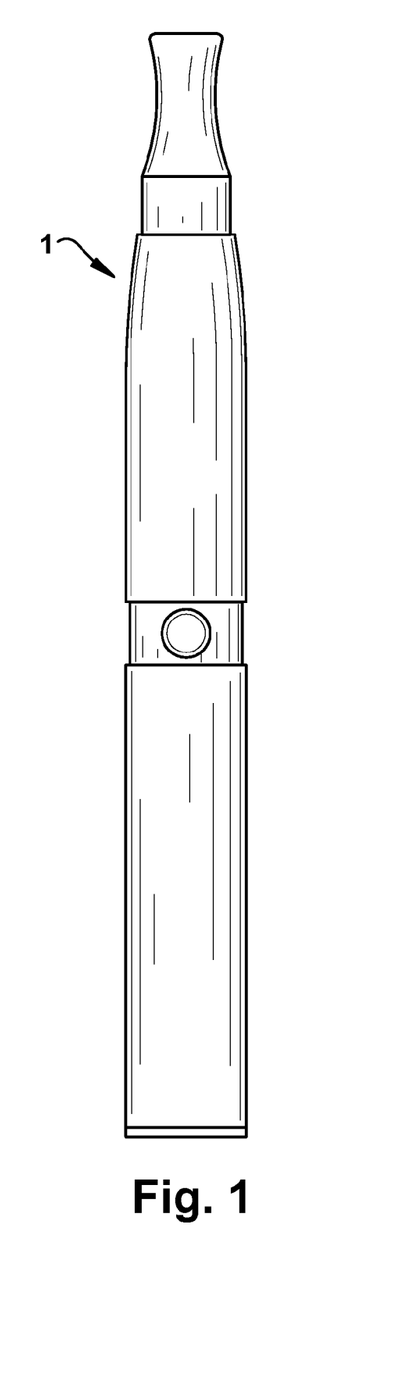
FIG. 1 shows a schematic drawing of one example type of vaporizer pen.
Figure 2:
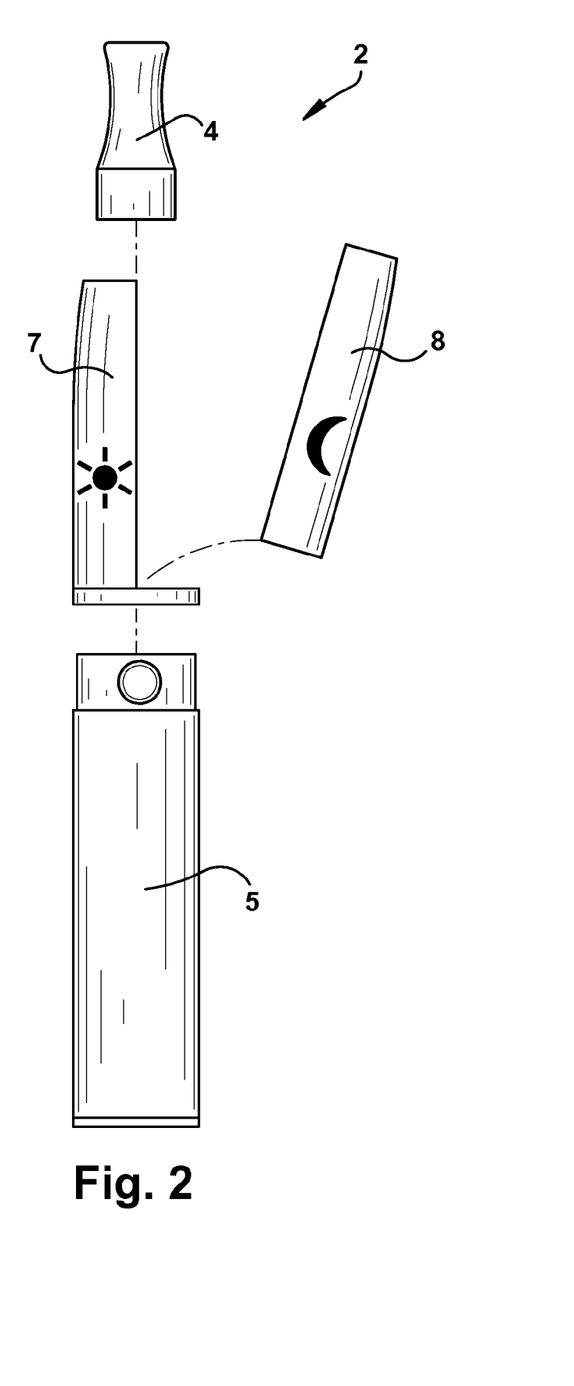
FIG. 2 show a schematic drawing of an example vapor delivery device that is separated into a base unit, a nozzle, and a pair of replaceable cartridges.

FIG. 1 is a drawing of an example of a vaporizer pen 1 that uses a single cartridge, and FIG. 2 shows a schematic drawing of a similar vaporizer pen 2 that is shown separated into separate components including a base 5, a nozzle/mouthpiece 4, and a pair of cartridges 7 and 8 that can provide different formulations of medication or other source materials for vaporization. Such devices can be used for dispensing formulations of one or more drugs, herbs, and/or other substances to a user for medicinal or recreational use.

Figure 3:
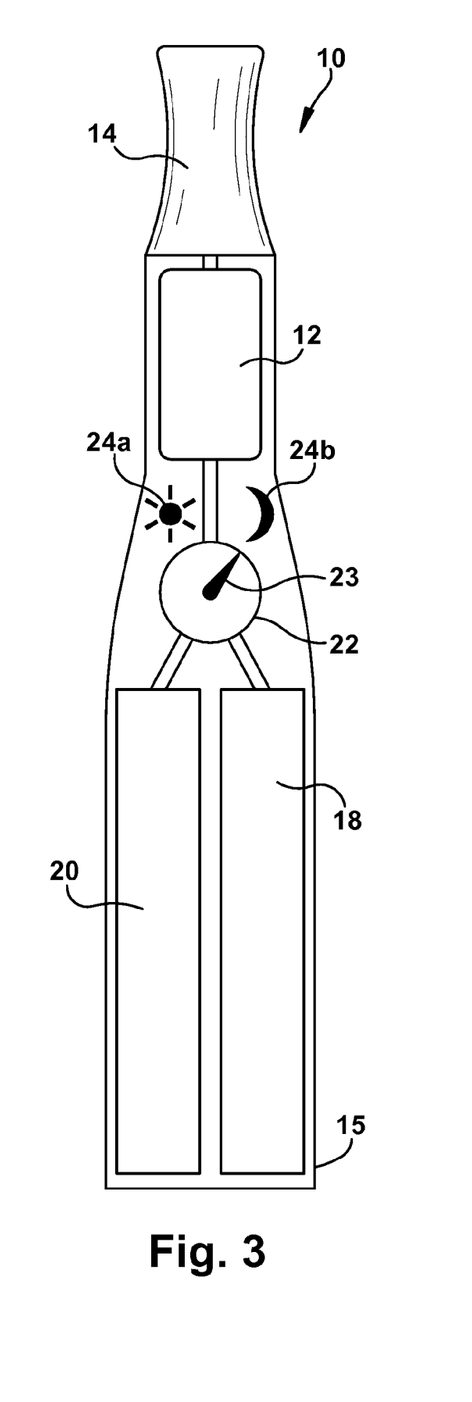
FIG. 3 shows a schematic drawing of an example embodiment of a vapor delivery device with its outer body in phantom, showing an internal chamber that can hold two cartridges and a selecting component for selecting the dosing cartridge.

FIG. 3 shows another example embodiment of a vaporizing device 10 provided in a schematic shown with a housing in phantom showing the internal components of the device 10. This device 10 has a nozzle 14 as an example dispensing component that is configured for dispensing a vapor orally to a user, and which may be removable and replaceable. The device 10 has a heating element 12 as an example vaporizing component that is provided in the upper body (case) 16 that provides a vaporized formulation to the nozzle 14. A base 15 is provided that can hold at least two dispensing tanks (or cartridges) 18, 20, which are examples of containers, each of which can be filled with a different formulation (e.g., of a drug, recreational substance, tobacco product, herb, etc.) for dispensing to a user. The device may use tanks as the containers that are not removable but are refillable, and that can be separately filled with the desired contents, or they may use replaceable cartridges that are pre-filled. Alternatively, the base 15 may come preloaded with the cartridges 18, 20, where the entire base and cartridges can be replaceable as a unit.

Switch 22 is provided as a selecting component to switch between the tanks/cartridges 18, 20, based on a selection by a user. An indicator 23 is provided on the switch for pointing to symbols 24a or 24b which act as indicia to show which tank/cartridge is connected as the current source of vapor, in this case by showing a sun 24a for daytime formulations vs. and moon 24b for nighttime formulations. Other symbols could be used, and in some cases replaceable symbols (such as by using stickers or tabs) can be provided to the user so that the user can appropriately associate the symbol with the cartridge. Also, such replaceable symbols or textual indicia may be provided by a seller or re-filler of the cartridges/tanks. Note that the pen 10 can be further adapted to utilize more than 2 tanks/cartridges, if desired, such as by supporting 3 or 4 such containers.

Users may purchase the replaceable cartridges (or the integrated replaceable base), or the user may have the cartridges refilled, by using a vendor that supports such filling and/or replacement, or the user may fill the cartridges with the user's own formulations using appropriate filling equipment. Generally, most users will likely purchase individual pre-filled cartridges filled with their desired formulations.

Generally, if replaceable cartridges are used, it is desirable to allow the cartridges 18, 20 to be separately replaceable, so that if one is exhausted it can be replaced independently of the other, although some embodiments where the separate tanks are integrated into a single replaceable unit are also contemplated. For example, as discussed above, the entire base 15 may be replaceable as an integrated unit with two or more tanks already installed. Alternatively, if permanently installed refillable tanks are used, it would be useful to allow each tank to be individually filled, such as by providing a filling interface (not shown) to each one of the tanks.

Note that an alternative device could be arranged using components similar to those of FIG. 3 such that the tanks/cartridges are provided near the nozzle and the heating (vaporizing) element provided in the base portion, which basically swaps items 18, 20 for item 12. Alternatively, the heating element may be provided as an integral part of each tanks/cartridges.

Note that a power source for the heater/vaporizer will likely be provided. Such a power source is known in the art, and may include one or more batteries, a fuel source (e.g., butane), or some other energy source to power the heater/ vaporizer. Furthermore, the vaporizer could utilize mechanical vaporization, rather than heat, to vaporize the formulation, or some other method of vaporization might be provided, such as combustion, boiling, etc.

Furthermore, as discussed above, the device can be adapted such that more than two tanks/cartridges are provided with a switch with at least a corresponding number of positions, such that a plurality of more than two formulations could be utilized. Such a device could administer different formulations of drugs or other substances based on time, for example, so that a person gets the proper drug and/or dosage at the proper time during the day and/or night. In such cases, the indicator indicia may show time periods, portions of the day, day and night indications (e.g., sun and moon) or may be numbered from 1 to the number of tanks/cartridges provided, for example. Textual indicia that names the drugs or formulations may also be provided. The indicia might be permanently attached, or removable and replaceable. Alternatively, the indicia could be provided using an electronic screen, such as LCD, for example. But in any case, the indicator indicia can help the user know which formulation is being administered at any given time, so that the proper formulation is being taken at the proper time.

In some embodiments, the selecting component may be selectable to mix formulations from more than one container, so that the device itself can provide a desired unique formulation of the container contents. In this case, the selecting component must be able to mix the different sources into a common output.

Figure 4:
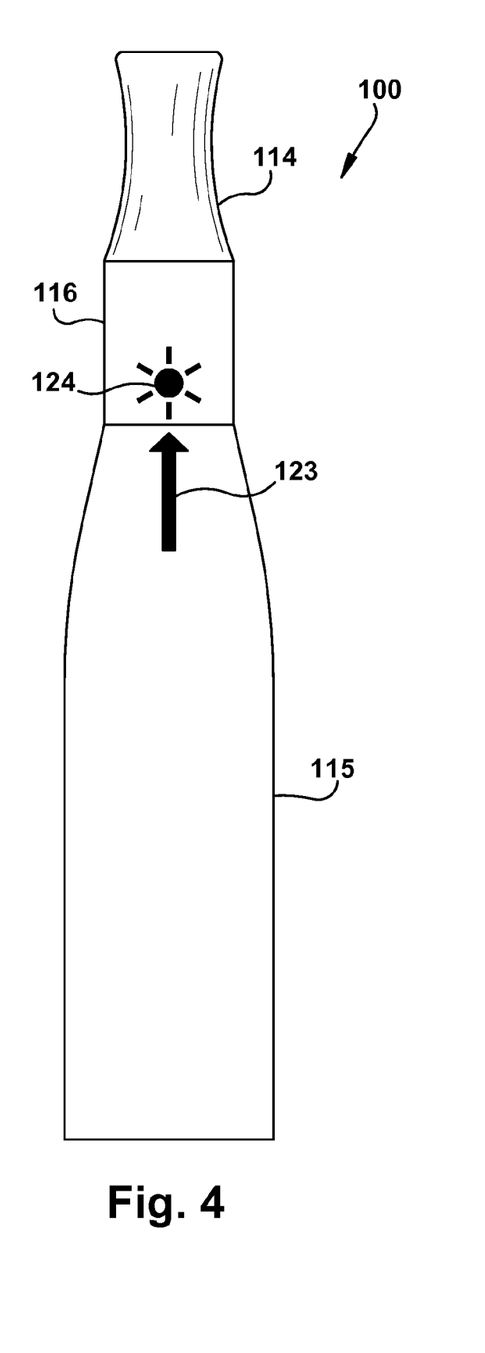
FIG. 4 shows a schematic drawing of another example embodiment of a vapor delivery device that has a twist function for selecting one of a plurality of dosing cartridges or tanks provided therein.
Figure 5:
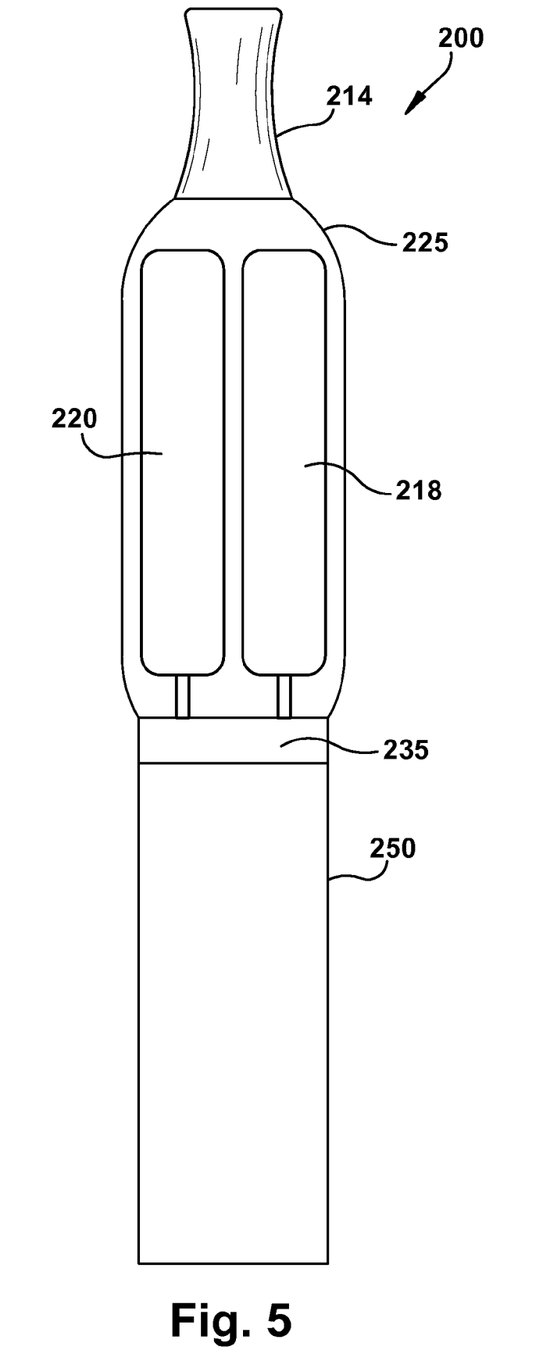
FIG. 5 shows a schematic diagram of an example embodiment of a vapor delivery device having two dosing cartridges or tanks.

FIG. 4 shows an alternative vaporizing device 100 with a nozzle 114 as the example dispensing component, a body 116, and an indicator 122, such that the selected dispensing tank (via a dispensing component, not shown) is chosen by twisting the device, rather than turning a switch. Such a twisting function is used on some pens for extending and retracting the pen tip, or use by pen flashlights for turning the flashlight on or off. Similarly, by twisting the device, one can select from any number of source formulations provided in different cartridges or tanks. Indicia can be printed directly on the body of the device as shown in the figure, for example, to clearly distinguish one formulation from another, so that the wrong formulation is not taken. Replaceable indicator indicia, as discussed above, could also be utilized, as could an electronic display. This device can utilize similar components internally as shown in FIG. 3, or may use an approach such as shown in FIG. 5, discussed below. Alternative means of selecting a desired container formulation could utilize electronic controls, where the selecting component is electrically controlled by a user interface, for example.

FIG. 5 shows another alternative device 200 in which a conventional base 250 can be used with a dispensing portion 225 holding two tanks/cartridges 218, 220. The tanks/cartridges may be individually replaceable, or the entire dispensing portion 225 with the tanks/cartridges may be replaceable as a unit. A selecting component (not shown) will be provided, such as in section 235, to select between one tank/cartridge and the other tank(s)/cartridge(s), such as by using a twisting feature similar to that of the example embodiment of FIG. 4, or a switch such as used for the example embodiment of FIG. 3.

Note that as an alternative or as an addition, to the above approach, different settings could be used to administer different amounts of a given formulation. Hence, one setting might be used to administer a first quantity of a formulation, whereas a second setting might administer a second larger or smaller quantity of the same formulation (thereby using the same cartridge/tank for both of these settings). And it is feasible to have some settings administer different dosages of the same formulation, with other settings administering different formulations in any desired combination. Further, some settings may mix various amounts of the formulations to achieve unique formulations.

Hence, in this manner, any of the above example devices can be used to support the administration of a variety of drug formulations through the use of multiple cartridges or tanks, each of which can contain a different formulation of drugs or herbs and/or a different dosage of a drug or herb. Appropriate indicators with indicia can be provided to identify the selected formulations (such indicia might be provided by the vendors selling the respective formulations). The user merely selects the proper setting using the provided switch and indicators for administering the currently desired formulation, ensuring that the proper formulation is administered at the desired time, and avoiding mistakes.

For example, a user may take one heart medication in the morning, and a different heart medication before bed. This can be accomplished by using two different cartridges, one for each heart medication, along with an indicator on the device that might, for example, point to indicia showing a sun for the morning, and a moon for the bedtime formulations, for example.

For medical marijuana users, different cartridges can be used for different strains of the plant for different effects. For example, the *Cannabis Sativa* strain of marijuana is associated with more energetic and uplifting effects, and hence is a strain best adapted for daytime use. In contrast, the *Cannabis Indica* strain has mellowing, relaxing effects that can lead to sleepiness, and hence may be more appropriate for evening and nighttime use. At least one other strain of marijuana, *Cannabis Ruderalis*, also exists, but that tends to be less sought after for medical uses. Each of these strains may be indicated for different medical conditions, and hence may be desirable for different times and doses. Furthermore, different strains and hybrids of these strains can be developed to have still different effects. The vaporizer device is particularly useful for medical marijuana users because it can lead to better controlled dose measurements and more discrete applications.

Or a diabetic may need to take a first medication in the morning, a second different medication at noon, and a larger dose of the morning medication in the evening. This can be accomplished through the use of three different cartridges, and an indicator that indicates three indicia values, such as "morn" "noon" and "night" for example, or "1" "2" "3" to show the administration sequence. Or alternatively, setting one might administer the first medication at a first dosage, and the third setting might administer the first medication at a second, larger dosage by administering more of the same formulation used for the morning dosage, in which case only two cartridges would be necessary.

Figure 6A:
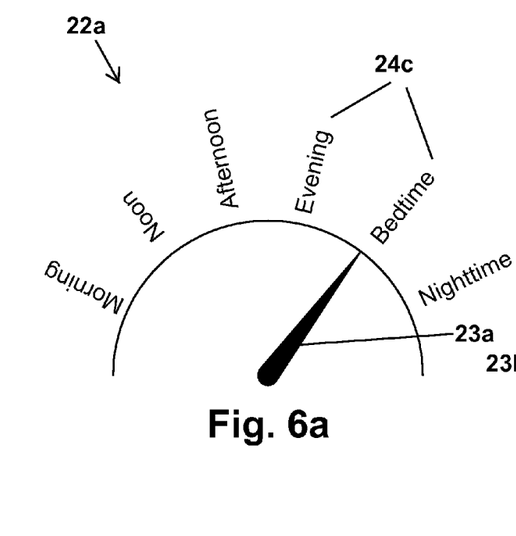
FIGS. 6a and 6b show two examples of indicators with indicia for indicating a formulation or dosage to be administered by a vapor delivery device.
Figure 6B:
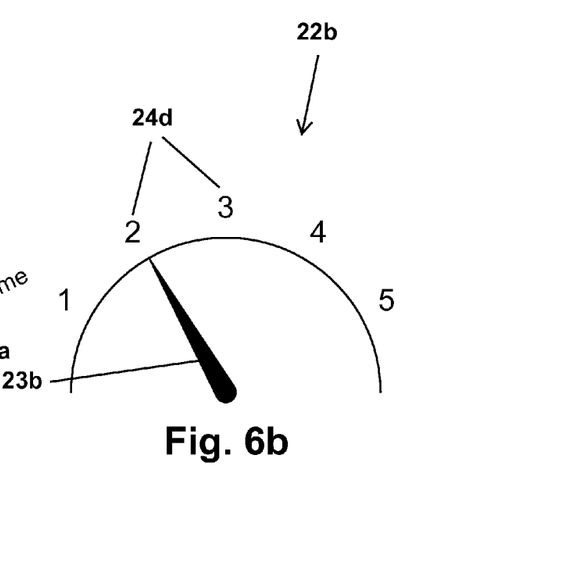

The indicators might be user selectable, for example, such as by providing a dial, or some other device that lets the user select the displayed indicator to differentiate the different formulations and their proper administration times. FIGS. 6a and 6b show two examples of switches 22a, 22b with indicators 23a, 23b, with indicia 24c, 24d, respectively, for indicating a formulation or dosage to be administered. FIG. 6a shows an indicator with indicia 24c differentiating among different times of day, whereas FIG. 6b shows an indicator with numeric indicia 24d to indicate which cartridge/tank or which dosage is being administered. Although the displayed indicators are shown using a rotating switches 22a, 22b similar to that used for the example device of FIG. 3, similar indicators and indicia could be used for the twist implementation of the device of FIG. 4. Of course, different types of indicators and indicia could be used, such as for listing the drug being administered, its dosage, or other information, as desired.

Figure 7A:
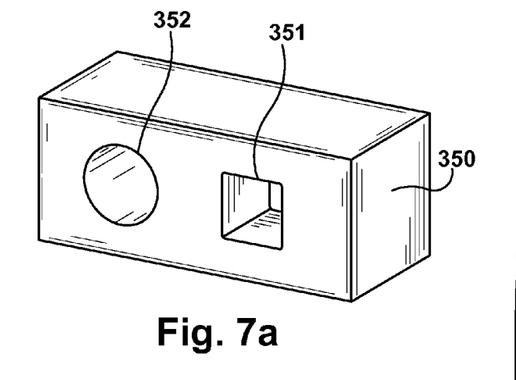
FIG. 7a shows a collar component with keyed receptors.
Figure 7B:
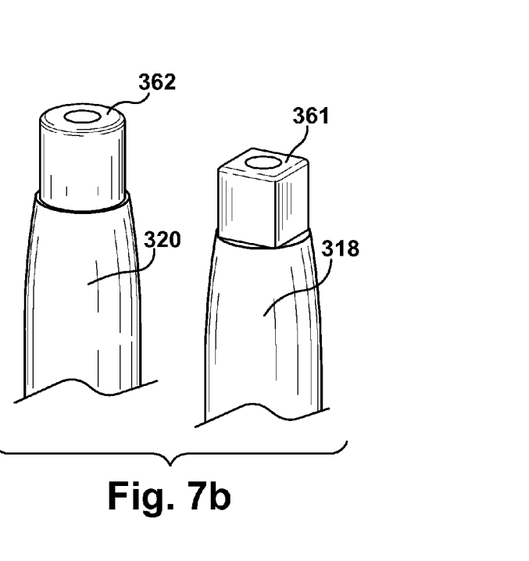

In order to ensure that formulations match the respective selection (e.g., selector/switch) locations, a means of ensuring that only appropriate cartridges with the appropriate formulations are installed at desired tank locations can be provided to better allow a user to ensure consistent control over selected formulations. FIGS. 7a, 7b shows one such means of matching desired cartridges/formulations to desired locations, through use of a collar 350. Insertion locations can be provided with unique geometric shapes so that are keyed so that only the appropriate cartridges will fit in the respective installation location. In the example of the collar of FIG. 7a, a square key hole receptor 351 and a round key hole receptor 252 are provided that match with the square neck 361 and round neck 362 of cartridges 318, 320, respectively, shown in FIG. 7b. Hence, the different shapes act to key specific cartridges to specific locations, so that the selecting components can properly identify respective formulations. In this case, the round key hole 352 and round neck 362 should have a diameter slightly larger than the length of a side of the square 351 to avoid a mismatch.

Hence, for example, a nighttime formulation might be provided using the round key, whereas a daytime formulation may be provided using the square key, such that when the selecting component is set to select the cartridge matched with the round key, a "moon" indicia may be provided on the indicator, and similarly when the selecting component is set to select the cartridge matched with the square key, a "sun" indicia may be provided on the indicator. Alternatively, specific drug formulations could be indicated using different indicia symbols, or names of the drugs.

Alternatively, a base can be provided with differently shaped key receptors matched to the respective bases of similarly shaped cartridges to act as the "keys" to ensure that the appropriate formulations are provided in the appropriate locations. Other mechanism to "key" specific cartridges to specific locations could include using body shapes of the cartridges matched to shapes in the portion of the chamber receiving them, for example.

Note that to ensure that the user does not accidently transpose formulations, the device may have replaceable indicia components provided to match with specific selector locations such that each indicator location is matched to a specific receptor shape to act as a "key" to ensure that the indicia are properly matched with their respective formulations.

Generally, the device is useful to provide a method of dispensing particular formulations of drugs (whether recreational, such a tobacco, or medicinal, such as marijuana), to a user to achieve a desired physical effect. For example, one formulation of tobacco may include a much higher dose of nicotine for use during the day (to provide a large stimulative effect), and a lower dose of nicotine for use during the night (for less stimulation). The nighttime dose may even provide one or more calming herbs (e.g., chamomile and/or valerian root) to aid in sleep. Hence, the different formulations will provide the user with vapors that have different physical (and/or mental) effects on the user. The device can then be used to dispense these different formulations as selected by the user.

For medical marijuana users, different formulations can be achieved using different strains of marijuana to provide different medical effects. For example, the *Cannabis Sativa* strain of marijuana is associated with more energetic and uplifting effects, and hence is a strain best adapted for daytime use. In contrast, the *Cannabis Indica* strain has mellowing, relaxing effects that can lead to sleepiness, and hence may be more appropriate for evening and nighttime use. At least one other strain of marijuana, *Cannabis Ruderalis*, also exists, but that tends to be less sought after for medical uses. Each of these strains may be provided for different medical conditions, and hence may be desirable for use different times and doses. Furthermore, different strains and hybrids of these strains can be developed to have still different effects. Hence, different formulations of the drug can be provided for different physical effects, as desired, with the user able to choose between at least two different such formulations using one of the example devices.

Other drug formulations can also be provided, such as drugs for treating depression, diabetes, asthma, pain, or some other physical ailment. Note that different formulations of any given drug might be provided for different times of the day or for different situation (i.e., an asthma dosage for regular use, and one for emergency use during an asthma attack, which may use the same drugs at different dosages, or even use different drugs). Alternatively, the device may be used to support formulations for completely different ailments, such as a formulation for administering a heart medication once daily, and a cholesterol medication, twice daily.

Generally, the user will purchase pre-filled cartridges with formulations prepared to provide the desired physical effect from appropriate vendors. To ensure proper drug formulations, the device may require specific cartridge types with associated indicia in order to ensure that the user knows which drugs are being dispenses. Hence, tight coordination between the device manufacturer and the cartridge supplier may be desirable for this reason.

Many other example embodiments can be provided through various combinations of the above described features. Although the embodiments described hereinabove use specific examples and alternatives, it will be understood by those skilled in the art that various additional alternatives may be used and equivalents may be substituted for elements and/or steps described herein, without necessarily deviating from the intended scope of the application. Modifications may be necessary to adapt the embodiments to a particular situation or to particular needs without departing from the intended scope of the application. It is intended that the application not be limited to the particular example implementations and example embodiments described herein, but that the claims be given their broadest reasonable interpretation to cover all novel and non-obvious embodiments, literal or equivalent, disclosed or not, covered thereby.

What is claimed is:

1. A method of dispensing a vapor, comprising the steps of:

providing a portable vapor dispensing device adapted for personal use, said portable vapor dispensing device comprising:

a dispenser configured for dispensing a vaporized formulation orally to a user, a vaporizer including a heating element, said vaporizer having a particular fluid connection input, a first container having a particular fluid connection output, a second removable container having another particular fluid connection output, and a switch configured for fluidly connecting the same vaporizer particular fluid connection input to a selected one of the first container particular fluid connection output or the second container particular fluid connection output for heating by the same heating element;

filling the first container with a first formulation for inducing a first physical effect in a user;

filling the second container with a second formulation for inducing a second physical effect in the user, said second physical effect being different than said first physical effect;

selecting one of the first formulation from the first container or the second formulation from the second container using the switch;

vaporizing, using the vaporizer, the selected one of the first formulation or the second formulation; and dispensing, using the portable vapor dispensing device, the vaporized selected formulation in a manner that can be inhaled by the user.

2. The method of claim 1, wherein said first drug formulation is configured for inducing drowsiness in the user whereas said second drug formulation is not configured for inducing drowsiness in the user.

3. The method of claim 1, wherein said first drug formulation includes formulation of marijuana strains, and where said second drug formulation includes a different formulation of marijuana strains.

4. The method of claim 1, wherein the vaporizer is provided between said dispenser and said switch for vaporizing either drug formulation that is selected.

5. The method of claim 1, wherein the portable vapor dispensing device further comprises a third container including another drug formulation, where said switch is further configured for connecting the dispensing device to the drug formulation included in the third container when selected.

6. The method of claim 1, wherein the portable vapor dispensing device has a chamber that is keyed for receiving the first container in a first location but not in a second location and the second container in the second location but not in the first location.

7. The method of claim 6, wherein the switch is provided with an indicator configured to point to indicia that identifies the formulation of the first container and also indicia that identifies the formulation of the second container.

8. The method of claim 7, wherein the indicia are replaceable and are provided with the associated formulation by a seller of that formulation.

9. A portable vapor dispensing device, comprising:
a dispenser configured for dispensing a vaporized formulation orally to a user,
a vaporizer,
a chamber configured to receive a removable first container specially configured to be installed only in a first location and a removable second container specially configured to be installed only in a second location, such that said chamber and containers are further configured such that said first container cannot be installed in said second location when not installed in said first location and when said second location is empty, and said second container cannot be installed in said first location when not installed in said second location and when said first location is empty; and
a switch configured for connecting the vaporizer to a selected one of the first container or the second container, wherein said vaporizer vaporizes the selected one of the first formulation or the second formulation to provide to said dispenser to dispense the vaporized selected formulation in a manner that can be inhaled by the user.

10. The device of claim 9, wherein said switch includes an indicator with associated indicia for indicating to the user which of the first formulation or the second formulation is currently selected.

11. The device of claim 9, wherein said chamber is keyed to receive the first container in the first location but not in the second location, and wherein said chamber is keyed to receive the second container in the second location but not in the first location.

12. The device of claim 9, wherein said first container and said second container are each separately replaceable cartridges.

13. The device of claim 9, wherein said chamber is comprised in a replaceable part integrated with said first container and said second container.

14. The device of claim 9, wherein at least one of said first container or said second container are refillable by the user.

15. A method of dispensing a vapor, comprising the steps of:
providing a portable vapor dispensing device adapted for personal use,
said portable vapor dispensing device comprising:
a dispenser configured for dispensing a vaporized formulation orally to a user,
a vaporizer with a heater having a particular fluid input,
a first container having a particular fluid output,
a second container having another particular fluid output, and
a switch configured for fluidly connecting the same vaporizer particular fluid input to a selected one of the first container particular fluid output or the second container particular fluid output for vaporizing using the heater, and
providing the first container with a first drug formulation;
providing the second container with a second drug formulation different than the first drug formulation; and
providing an indicator on the vapor dispensing device associated with the switch, said indicator indicating a first indicia identifying that the first formulation from the first container has previously been selected and also indicating a second indicia identifying that the second formulation from the second container has previously been selected.

16. The method of claim 15, said portable vapor dispensing device further comprising a chamber configured to receive the first container specially configured to be installed in a first location and the second container specially configured to be installed in a second location, such that said chamber is further configured such that said first container cannot be installed in said second location, and said second container cannot be installed in said first location.

17. The method of claim 15, further comprising the steps of:
filling the first container with a first formulation for inducing a first physical effect in a user; and
filling the second container with a second formulation for inducing a second physical effect in the user, said second physical effect being different than said first physical effect.

18. The method of claim 17, further comprising the steps of:
selecting one of the first formulation from the first container or the second formulation from the second container using the switch;
vaporizing, using the vaporizer, the selected one of the first formulation or the second formulation; and
dispensing, using the dispenser, the vaporized selected formulation in a manner that can be inhaled by the user.

19. The method of claim 18, said portable vapor dispensing device further comprising a chamber configured to receive the first container specially configured to be installed in a first location and the second container specially configured to be installed in a second location, such that said chamber is further configured such that said first container cannot be installed in said second location, and said second container cannot be installed in said first location.

20. A method of dispensing a vapor, comprising the steps of:
providing a portable vapor dispensing device adapted for personal use,
said portable vapor dispensing device comprising:
a dispenser configured for dispensing a vaporized formulation orally to a user,
a vaporizer including a single heater having a fluid input,
a first container having a particular fluid output,
a second removable container having another particular fluid output, and
a switch configured for fluidly connecting the vaporizer fluid input to a selected one of the first container particular fluid output or the second container particular fluid output wherein said switch includes an indicator for indicating which of the first container or the second container is currently selected;
filling the first container with a first formulation for inducing a first physical effect in a user;
filling the second container with a second formulation for inducing a second physical effect in the user, said second physical effect being different than said first physical effect;
selecting one of the first formulation from the first container or the second formulation from the second container using the switch;
vaporizing, using the single heater, the selected one of the first formulation or the second formulation; and
dispensing, using the portable vapor dispensing device, the vaporized selected formulation in a manner that can be inhaled by the user.

21. A portable vapor dispensing device, comprising:
a dispenser configured for dispensing a vaporized formulation orally to a user,
a chamber configured to receive a removable first container specially configured to be installed in a first location and a removable second container specially configured to be installed in a second location, such that said chamber is further configured such that said first container, when not installed in said first location, cannot be installed in said second location when said second location is empty, and said second container, when not installed in said second location, cannot be installed in said first location when said first location is empty; and
a switch configured for selecting one of the first container or the second container according to a switch position, wherein
said portable vapor dispensing device dispenses the selected formulation in a manner that can be inhaled by the user.

22. A portable vapor dispensing device, comprising:
a dispenser configured for dispensing a vaporized formulation orally to a user,
a chamber configured to receive a removable first container specially configured to be installed in a first location by a first keyed structure matching said first location and a removable second container specially configured to be installed in a second location by a second keyed structure differently keyed than said first keyed structure, wherein
said portable vapor dispensing device dispenses the vapor in a manner that can be inhaled by the user.

23. A portable vapor dispensing device adapted for personal use, comprising:
a dispenser configured for dispensing a vaporized formulation orally to a user,
a vaporizer including a heating element, said vaporizer having a particular fluid connection input,
a first removable container having a first fluid connection output,
a second removable container having a second fluid connection output, and
a switch configured for fluidly connecting the same vaporizer particular fluid connection input to a selected one of the first container particular fluid connection output or the second container particular fluid connection output for heating by the same heating element for outputting a vaporized formulation to the dispenser.

* * * * *